United States Patent [19]

Cole

[11] Patent Number: 5,707,850

[45] Date of Patent: Jan. 13, 1998

[54] CONCENTRATION AND SIZE-FRACTIONATION OF NUCLEIC ACIDS AND VIRUSES IN POROUS MEDIA

[76] Inventor: Kenneth D. Cole, 9200 Tulip Grove, Gaithersburg, Md. 20879

[21] Appl. No.: 555,443

[22] Filed: Nov. 9, 1995

[51] Int. Cl.⁶ .................................................. C12N 5/00
[52] U.S. Cl. ................................. 435/239; 536/25.4
[58] Field of Search .......................... 435/239, 235.1, 435/261

[56] References Cited

PUBLICATIONS

Alberts et al. *Molecular Biology of the Cell*. 1983, pp. 173–176 & 189.

Wu–Pong, "Oligonucleotides: Opportunities for Drug Therapy and Research," BioPharm, Nov. 1994, pp. 20–30.

Marquet et al., "Process Development for the Manufacture of Plasmid DNA Vectors for Use in Gene Therapy," PioPharm, Sep. 1995, pp. 26–37.

Marshall, "Gene Therapy's Growing pains," Science, vol. 269, Aug. 1995, pp. 1050–1055.

Turerk et al., "Systematic Evolution of Ligands by Exponential Enrichment: RNA Ligands to Bacteriophage T4 DNA Polymerase," Science, vol. 249, Aug. 3, 1990, pp. 505–510.

Porath, "Column Electrophoresis on a Large Scale," Science Tools, Aug. 1964, pp. 21–27.

*Primary Examiner*—Leon B. Lankford, Jr.
*Attorney, Agent, or Firm*—Jagtiani & Associates

[57] ABSTRACT

The present invention relates generally to separation methods, and more particularly to a method to separate nucleic acids and viruses from other substances using porous media by combining flow rate and with electrical field strength. For example, methods to concentrate and size-fractionate of nucleic acids are hereby provided.

17 Claims, 9 Drawing Sheets

CONCENTRATION AND SIZE-FRACTIONATION OF NUCLEIC ACIDS AND VIRUSES IN POROUS MEDIA

BACKGROUND OF THE INVENTION

Field of the Invention

The present invention relates generally to separation methods, and more particularly to a method to separate nucleic acids and viruses from other substances using porous media by combining flow rate and with electrical field strength. For example, methods to concentrate and size-fractionate of nucleic acids are hereby provided.

Large scale separations of nucleic acids are important in the biotechnology industry as well as the pharmaceutical industry. Currently, purified nucleic acids are used as research tools. In the future, purified nucleic acids will also be used as therapeutic agents themselves. A large number of human gene therapy clinical trials are currently underway. Marshall, 269 Science 1050 (1995). For instance, oligonucleotides designed to inhibit the expression of specific genes show promise as antiviral and anticancer agents. Wu-Pong, 7(9) BioPharm. 20 (November 1994). Moreover, RNA molecules selected from combinatorial libraries that are capable of high affinity binding to target molecules are an example of ligands that could be used therapeutically or for diagnostic purposes. Tuerk and Gold, 249 Science 505 (1990).

In addition to the development of nucleic acids as compounds, a variety of methods for introducing nucleic acids (i.e. viruses, cationic liposomes, DNA-protein complexes, and direct injection of DNA) into cells and tissues are currently being tested. Production of large amounts of plasmid DNA for these type of experiments is a new challenge in bioprocessing. Marquet et al., 8(7) BioPharm. 26 (1995). Likewise, removal of nucleic acids from genetically-engineered products will continue to be the focus of FDA inquiry, as well as a challenge to the pharmaceutical industry. Therefore, large-scale separations of nucleic acids is an important area of research now, and will be important in the future as new products are developed.

Separation of nucleic acids prior to the present invention has been limited to hydrodynamic methods (such as sedimentation through a density gradient), electrophoresis in a sieving media (such as a gel or in a polymer in a capillary), chromatography and ultrafiltration. Electrophoresis has proven to be a highly successful method for the separation of nucleic acids on an analytical scale. The most successful of these analytical methods, however, electrophoresis in gels or in capillaries, has limited the scale of the separations. Column chromatography using either adsorption or partition separation mechanisms has proven to be the most useful method for large-scale separations of nucleic acids, as well as proving to be an important analytical tool. Adsorption chromatography (ion-exchange) and partition chromatography (size-exclusion and reverse phase) are widely and successfully used to separate DNA on analytical and preparative scales. Marquet et al., 8(7) BioPharm. 26 (1995). Sedimentation of nucleic acids in density gradients requires the use of an ultracentrifuge, and thereby limits its commercial applicability.

The present invention uses porous media and a combination of flow and electrical field strength to separate nucleic acids. The combination of flow and electrical fields has been used in the field of electrochromatography.

Electrochromatography (EC) was originally developed for the scale-up of electrophoresis of proteins. The packing material in EC was regarded as an anti-convective media in which to do zone electrophoresis, and, due to this assumption, media that displayed the lowest adsorptive properties were used. Porath, 11 (2) Sci. Tools 21 (1964). Long periods of electrophoresis were necessary because of the low fields necessary to prevent heating. Later studies used simultaneous elution and electrophoresis for the separation of proteins. Nerenberg and Pogojeff, 51 Am. J. Clin. Path. 728 (1969); Luzzio, 4 J. Infect. Dis. 359 (1964). Rudge et al. renewed interest in EC by studying the mechanism of the separation process using Sephadex G-75. Rudge et al., 39 AIChE J. 797 (1993).

Very high electrical fields applied across a small diameter columns packed with non-porous materials have been used to separate bases and oligonucleotides. Tsuda, 59 Anal. Chem. 521 (1987); and Behnke and Bayer, 680 J. Chrom. A. 93 (1994). These systems are limited to small diameter columns and must be run under high pressure to minimize bubble formation due to the high fields applied. These systems are very different that the separations described in this study.

SUMMARY OF THE INVENTION

According to one broad aspect of the present invention, there is provided a method to separate nucleic acids from a mixture of components which includes nucleic acids in a porous medium comprising: introducing the mixture to be separated onto porous media in buffer; and applying an electrical field current to the porous media; and directing the flow of the buffer/mixture in such a manner that the mixture is separated into desired components.

Also provided is a method to separate viruses from a mixture of components which includes viruses in a porous medium comprising: introducing the mixture to be separated onto porous media in buffer; and applying an electrical field current to the porous media; and directing the flow of the buffer/mixture in such a manner that the mixture is separated into desired components.

It is therefore an object of the present invention to provide a which will provide method to concentrate nucleic acids.

It is a further object to provide a size fractionate nucleic acids.

Other objects and features of the present invention will be apparent from the following detailed description of the preferred embodiment.

DEFINITIONS

Separation—any partitioning of nucleic acid from other substances, including other nucleic acids.

Size-fractionation—the separation of nucleic acids into fractions that differ in size (molecular weight).

Concentration—the process of converting a dilute solution into a solution less dilute.

Porous—a media that may appear as either solid, granular or membranous and consist of beads, particles, or solids. The media contains pores or channels that allow a fluid such as water or aqueous solution to flow through the media being driven by a pressure difference between the inlet and the outlet. The media itself may be permeable or impermeable to macromolecules, ions, and water.

Negative field—the configuration in which the positive electrode is at the solution inlet and the negative electrode is at the solution outlet.

DETAILED DESCRIPTION OF THE INVENTION

The present invention provides methods to separate nucleic acids from solutions by retention in porous media with low electrical fields. A large volume of nucleic acid can be concentrated on the porous media by the electrical field. Other components in the mixture (e.g. proteins, carbohydrates, lipids, etc.) are not as strongly retained by the weak electrical field and elute from the porous media with the solution. When the electrical field is reduced or removed, the nucleic acid elutes in a concentrated zone.

Nucleic acid can be concentrated and size fractionated by this technology. The retention of nucleic acid is dependent upon the flow of the solution and the electrical field strength using a given porous media. By varying these two variables (flow and electrical field) beyond the parameters necessary for separation from proteins and other cell components, size fractionation of nucleic acid is accomplished. Nucleic acid molecules of shorter length are not retained as strongly as longer nucleic acid by the porous media (with a given flow rate and electrical field). This allows selection of the length (size) of nucleic acid molecules that are fully retained in the porous media by adjusting the flow velocity and electrical field strength. The smaller nucleic acid moves faster through the column compared to longer nucleic acid for a given flow velocity and field strength. Therefore, the differential velocity and retention of nucleic acid molecules on the porous media is an effective way to size fractionate nucleic acid.

In particular, viruses can be retained on the porous media under the influence of an electrical field with flow. A virus can be concentrated on the porous media with a low electrical field with flow. The virus can then be removed from the porous media by reducing or shutting off the field. There is a unique set of conditions (i.e., solution flow rate and electrical field strength) that will immobilize a virus using a given media and solution composition.

The technology uses flow through porous media with an applied electrical field. The electrical field causes the selective retention of nucleic acids. The retention of nucleic acids is dependent on the flow rate (velocity) and electrical field strength in a given porous media. The chemical and physical nature of the porous media is important part of the separation process. Very selective separations are possible using this technology because the electrical field strength, flow velocity, and porous media can be varied for each separation. Individual components in the mixture will be retained to varying degrees by the separation conditions used. The degree of retention is determined by the chemical and physical properties of each component.

The flow rate of the solution through the porous media is a important variable in this process. The flow rate can be held constant or varied. Flow rate can be changed in steps or continuously (a gradient) during the separation process.

The media must be porous, and preferably is fairly neutral. For example, Sephadex (dextran), cellulose based media, acrylamide-based, polymeric particles or porous silica can be used. The method is successful in a column using porous beads, but can also be done on could be accomplished on membranes, thin layers or similar apparatus, so long as the medium is porous.

The pH, ionic strength, and composition of the solution can also be modified during the separation process. The pH of the solution determines the charge and electrophoretic mobility of each component. It is possible to lower the pH significantly, so that the proteins will become positively charged and not be retained, while nucleic acids will still be negatively charged and retained on the porous media. The ionic strength and ionic composition of the solution will influence the electrical field strength and influence interactions of components with the porous media. The solution can be varied in its composition to include additives that vary the interactions of the components with the porous media (such as detergents and zwitterions). Modification of the composition of the solution during the separation is therefore a variable that can be used to achieve selective separations.

The electrical field strength and polarity can also be changed during the separation. The field can be changed continuously or in steps. Alternating and pulsed electrical fields can also be used. Any direction of pulsing may be used, including reverse flow, right angles, orthagonal, etc. Moreover, a negative field is preferred, although a positive field can also be used. The low fields used to separate the DNA are advantageous for several reasons. The low fields do not result in column heating which can lead to temperature gradients that ruin resolution and can denature delicate biological molecules. The low fields have very little effect on the retention of proteins so that they pass through the column.

Recovery of products can be automated, and therefore make the process commercially viable. The methods can be used for PCR product recovery, or to remove unwanted nucleic acids (including viruses) from biotech products. The process can also be used to separate nucleic acids from proteins, viruses from proteins, single-stranded DNA from double-stranded DNA, supercoiled nucleic acids from relaxed or nicked nucleic acids, and linear from circular forms.

The essential elements of the separation include a zone of porous media, electrodes for applying an electrical field across the media, a means of flowing solution through the porous media (such as a pump), a device to introduce sample to be separated (such as an injector), and a device to collect the solution.

Figure 2:
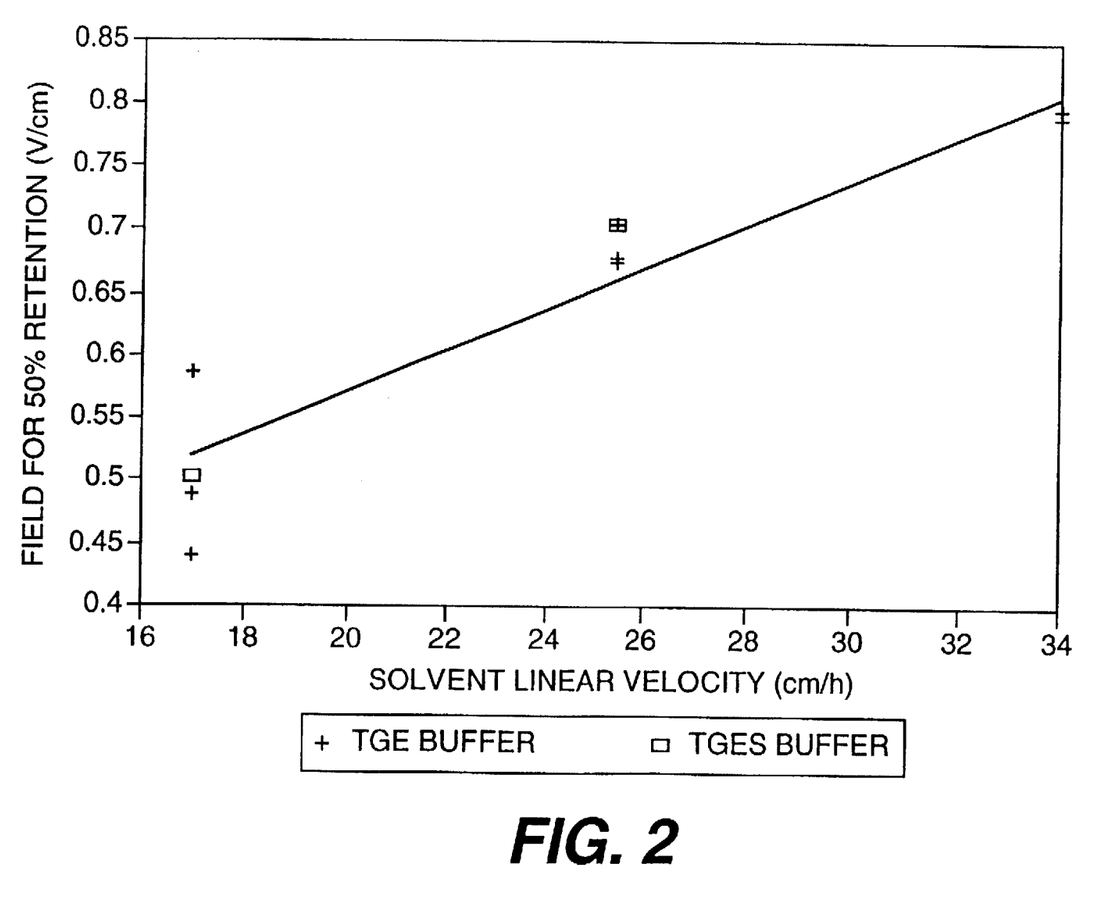

Three variables are important to size-fractionation of DNA: electrical field strength, buffer flow, and porosity of the chromatography media. The relationships shown in Table 1 and FIG. 2 show the dependence of electrical field strength and solution flow rate (velocity) on the retention of DNA. Higher flow rates require higher electrical field strength to retain the DNA. Very broad limits to the flow rate are 0.1–200 cm/hr. The field strength can be from 0.1–50 V/cm.

TABLE 1

The influence of Electrical Field Strength and Buffer Linear Velocity on Retention of DNA Restriction Fragments.

| Field (V/cm) | Velocity (cm/h) | Size of DNA Fragment Retained (Base Pairs) |
|---|---|---|
| 1.5 | 12.2 | >2000 |
| 3.1 | 12.2 | >500 |
| 4.8 | 12.2 | >300 |
| 3.1 | 8.6 | >400 |
| 3.1 | 15.9 | >600 |

EXAMPLES

Example 1

Concentration and Size Fractionation of DNA

Buffer Solutions and Conductivity Measurements

The buffer referred to as TGE was composed of 3.9 mM tris(hydroxymethyl)aminomethane (TRIS), 47 mM glycine, 0.25 mM ethylenediaminetetraacetic acid (EDTA) with a final pH of 8.2 (25° C.). The buffer referred to as TGES was TGE with 5 mM added sodium chloride. TGE has conductivity of 174 uS at 25° C. and TGES has conductivity of 758 uS at 25° C. TRIS base and glycine were made up as a 10-fold concentrated stock and EDTA as 0.5M pH 8.0 solution and diluted to the final concentrations described without adjustment of pH.

Electrochromatography Apparatus

Water jacketed columns, 15 or 25 mm, inside diameter, were thermostated at 25.0° C. Columns were obtained commercially (Ace Glass, Vineland, N.J.) or made of varying lengths by a glassblower using the same diameter tubing. The packing supports used at both ends of the columns were polyethylene (100 micron). The end fitting were specially modified end fitting contained platinum electrodes isolated from the solution streams by dialysis membrane molecular weight cutoff of 6,000 to 8,000, Spectrapor 1, Spectrum Medical Industries, Los Angeles, Calif.). A regulated power supply connected to a potentiometer was used for low voltage (less than 30 V) runs. After a few minutes of operation the current and voltage of the run did not change significantly during the run. The power supply was turned on a few minutes before sample application and turned off at the indicated times. A peristaltic pump (Minipuls 3, Gilson Medical Electronics, Middleton, Wis.) was connected to the outlet of the column and used to monitor flow. The eluent was monitored at 260 nm (Holochrome Detector equipped with 0.05 ml flow cell, Gilson Medical Electronics, Middleton, Wis.) and collected by a fraction collector. Flow was measured using a digital flowmeter (Phenomenex, Torrance, Calif.).

The electrical field strength (E) was calculated by the formula $E=I/A \cdot k$, where I is the current, A is the cross section area of the column, and k is the conductivity of the buffer or packed chromatography gel.

Materials

Bovine serum albumin (fraction V), Sephadex G-75 Regular (40–120 micron dry bead diameter), Sephadex G-25 Fine (20–80 μm dry bead diameter) and TRIS base were obtained from Sigma Chemical Co. (St. Louis, Mo.). Alu I, 1 Kb DNA ladder, and λ DNA (48,502 basepairs) were from Life Technologies (Gaithersburg, Md.). Blue Dextran 2000 was obtained from Pharmacia (Uppsala, Sweden).

Measurement of Electrophoretic Mobility and Fraction Analysis

The free-solution electrophoretic mobility of λ DNA and bovine serum albumin was determined by density gradient electrophoresis as described in Cole et al. 707, *J. Chrom.* 77 (1995). The gradient used was 1 to 35% sucrose in 1×TG buffer (no EDTA) and samples dissolved in 1 ml of 37% sucrose containing 1×TG and a trace of bromophenol blue. The electrophoresis conditions and calculations were as previous described (Cole et al., 707, *J. Chrom.* 77, 1995).

Gel Electrophoresis

DNA fractions were analyzed using gel electrophoresis in either agarose (0.75 or 1.5%) or acrylamide (8 or 12%) using 0.09M TRIS, 0.09M boric acid, 1 mM EDTA. The gels were stained in ethidium bromide (1 μg/ml) for 30 min and destained in water before transillumination and photography.

Conductivity Measurements

All of the chromatography media used had measured conductivities lower than the buffer they were equilibrated with. The lowest conductivity was for the more highly cross-linked Sephadex G-25 (approximately 50% of the buffer conductivity). A packed bed of Sephadex G-75 had a conductivity approximately 88% of the conductivity of the buffer. The TGES buffer with 5 mM added sodium chloride had a conductivity approximately 4.4 times the conductivity of the buffer TGE.

Free-Solution Electrophoretic Mobility Measurements

It was of interest to determine the electrophoretic mobility of DNA relative to that of proteins, since proteins required relatively large electrical fields to effect their elution behavior on electrochromatography columns. The measured free-solution electrophoretic mobilities of λ DNA and bovine serum albumin as measured in a sucrose density gradient described in Cole et al. 707, *J. Chrom.* 77 (1995). λ DNA has a mobility that is approximately 170% of the mobility of bovine serum albumin. Bovine serum albumin had the highest mobility of the proteins measured in a previous study (Cole et al. 1995).

Retention of DNA on Porous Media

Figure 1:
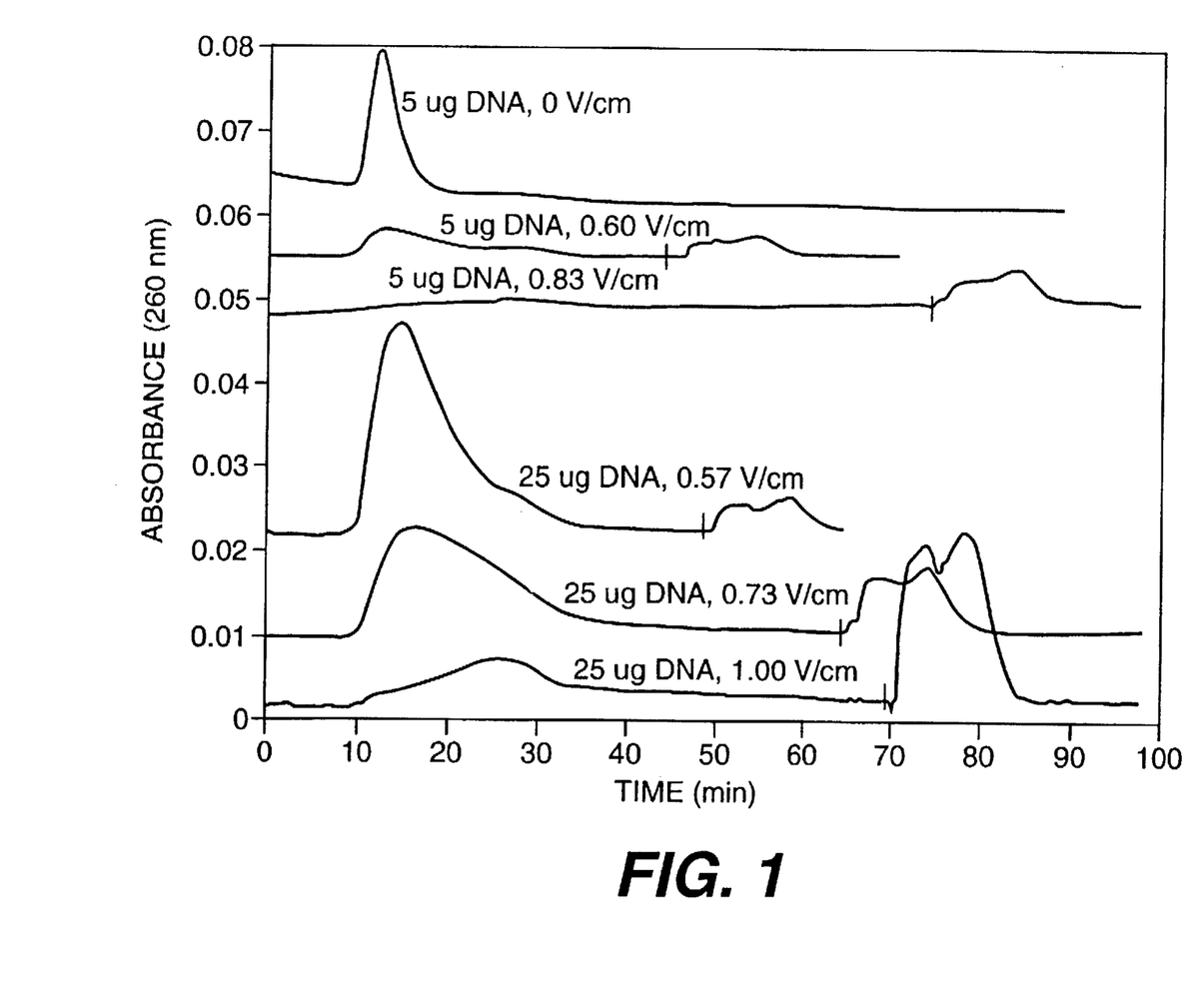

The retention of λ DNA on the column was determined by injecting a fixed amount of DNA at a constant buffer linear velocity and a given electrical field strength. The peak area of the DNA not retained was determined and then the field was then shut off and the peak area retained DNA was determined (FIG. 1). A series of DNA injections with different electrical filed strength was done to determine the influence of electrical field strength on DNA retention for a given flow rate. This data was used to calculate the electrical field strength that retains 50% of the peak area of the injected DNA at a given flow rate (FIG. 1). The DNA eluting after the electrical field was turned off had a complex peak shape. A fraction of the DNA eluted early after the field was removed and a fraction eluted with a delay time it would take to elute from the inlet of the column. This indicates that some of the DNA had moved down the column and some of the DNA had remained near the inlet of the packed bed.

Table 2 shows the electrical field strengths required for retention of 50% of injected λ DNA by negative field orientation. Electrical fields were calculated using the conductivity of the buffer.

TABLE 2

| Electrical Field for 50% Retention of 5.1 μg of λ DNA. Field (V/cm) | | |
|---|---|---|
| Linear Velocity (cm/hr) | Sephadex G-75 | Sephadex G-25 |
| 17.0 | 0.51 ± 0.06 (N = 3) | 1.56 ± 0.12 (N = 3) |
| 25.5 | 0.69 ± 0.01 (N = 3) | |
| 34.0 | 0.80 ± 0.01 (N = 3) | |

The dependence of electrical field strength to retain 50% of the injected DNA by buffer linear velocity (flow rate) is shown in FIG. 2 and Table 2. Higher electrical field strengths were required to retain the DNA at higher buffer linear velocities (flow rate). Increasing the loading of DNA by 5-fold (to 25 μg) required an increase in field strength of 33% (average of two determinations) higher than the field required to retain 5 μg DNA. The influence of gel porosity on the electrical field strength was determined by using the Sephadex G-25 which is more highly cross-linked with an exclusion limit of 5,000 (determined using dextrans). To retain λ DNA on Sephadex G-25 required a approximately a 3-fold higher field compared to Sephadex G-75.

Sephadex is known to have a small number of carboxyl groups which can cause ion-exchange adsorption. The manufacturer recommends buffers of at least 0.02M ionic strength be used to eliminate the possibility of ion-exchange. The TGES buffer with 5 mM added salt has 4.4 times the conductivity of TGE and would has a greater ionic shielding effect on the chromatography media compared to TGE buffer. The results shown in FIG. 2 indicate that there is no significant different between the two buffers in field strength required to retain the λ DNA The retention of λ DNA on Sephadex G-75 was very dependent upon the polarity of the electrical field. A positive field was not effective at retaining λ DNA (a 1.5×10.2 cm column packed with Sephadex G-75). A field of 14.2 V/cm retained approximately 30% of the 5 µg of λ DNA at a flow rate of 17 cm/hr. When positive fields were used the non-retained DNA peak was very broad and difficult to measure. The higher fields necessary to retain DNA with positive fields can also result in heating in the center of the column, which could cause peak broadening.

Concentration of DNA on Porous Media

Figure 3:
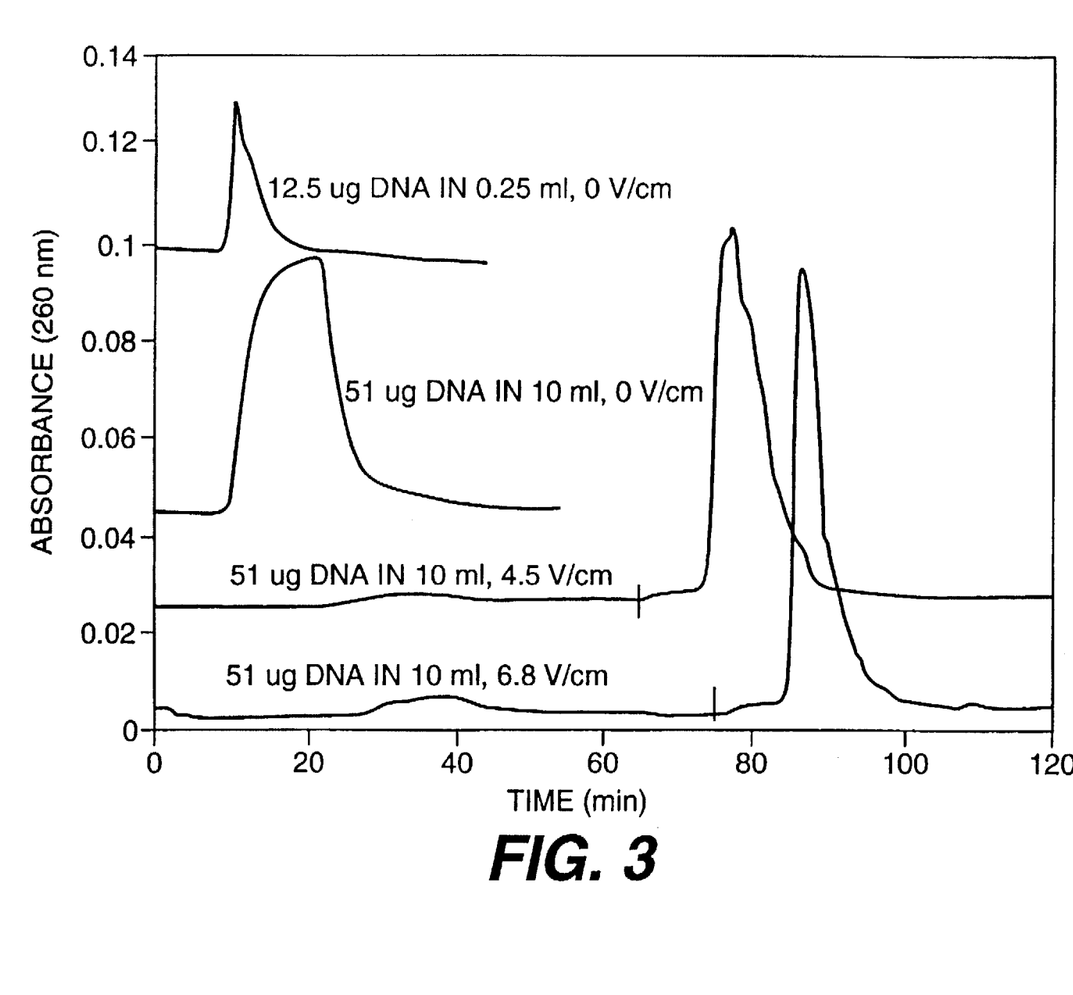

To demonstrate that DNA can be concentrated on the column a large volume (10 ml) of a dilute λ DNA solution was applied to the column (FIG. 3). Without an applied electrical field the DNA eluted as a broad peak. When the large sample was applied with an electrical field the DNA did not elute until the field was turned off. After the field was turned off the DNA eluted with a retention time (after subtracting the time the field was applied) and a peak shape the similar to DNA injected without a field on. A higher field resulted in a sharper peak of the retained DNA (FIG. 3). This result indicating that the DNA was retained at the inlet of the packed bed in a relatively narrow zone.

Size-Fractionation of DNA

A mixture of DNA fragments (Alu I restriction digest of λ DNA) was used to determine if size-fractionation of DNA was occurring in the column during EC. When the restriction fragment mixture was applied to the column in the absence of an applied field, the DNA fragments eluted with the excluded volume of the column.

Figure 4A:
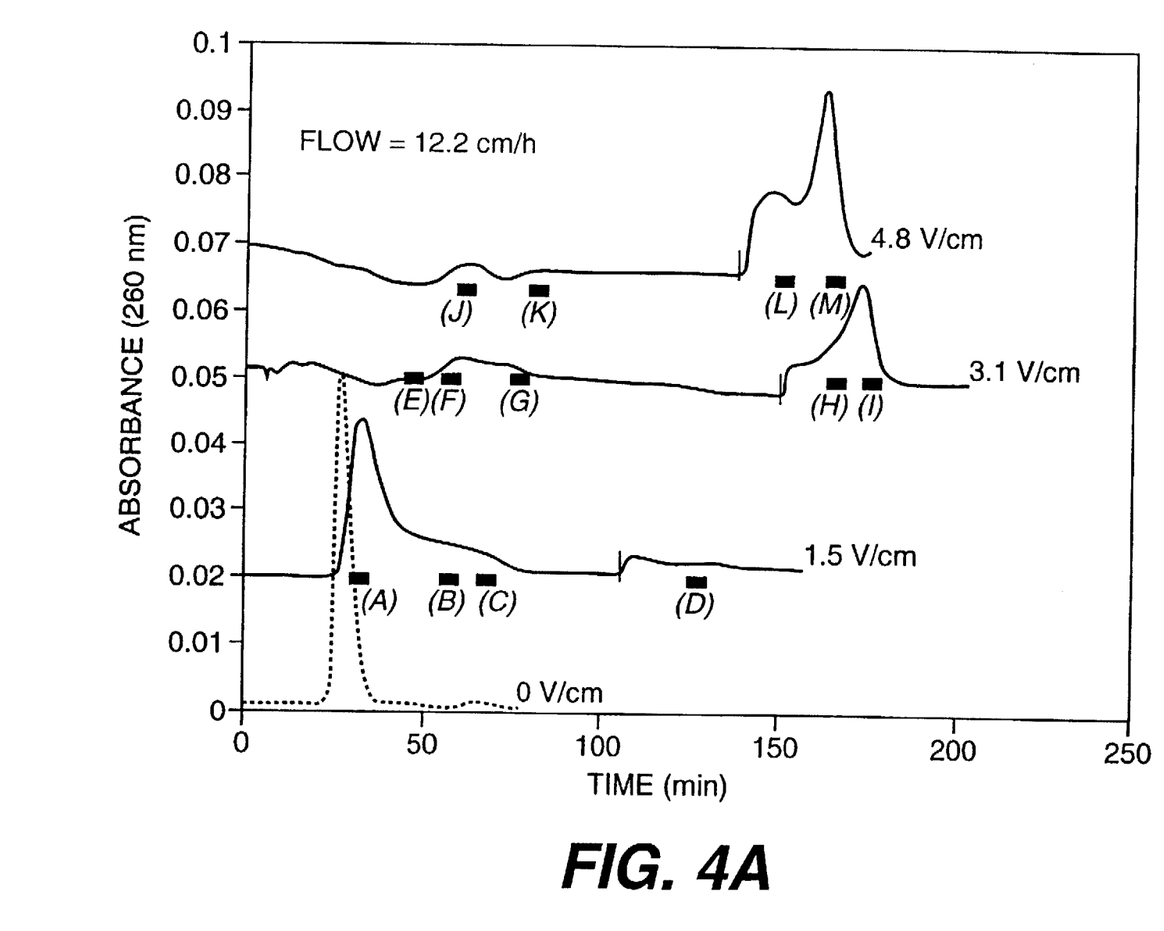
Figure 4B:
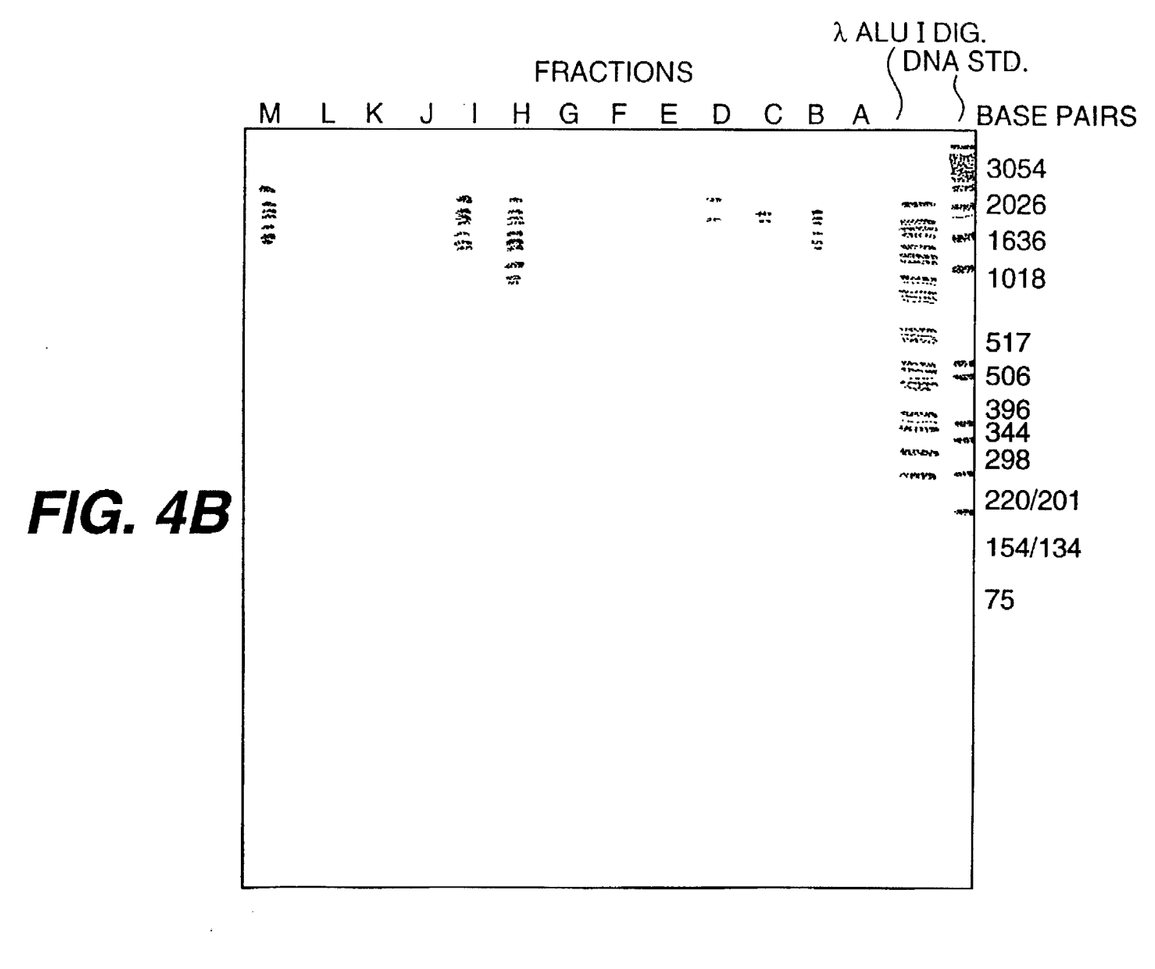

We examined the influence of flow rate and electrical field strength on the fractionation of the large number of restriction fragments. FIG. 4A and B shows the influence of changing the electrical field strength on the separation of the restriction fragments. The DNA fragments can be divided into three groups, those fragments not retained, those partially retained, and those fully retained on the column. The fragments not retained came out with the exclusion limit of the column, followed by fragments whose elution were slowed on the column. When the field was shut off another set of fragments that were retained came off the column. The fragments retained on the column also had a complex peak shape indicating movement on the column (FIG. 4A). The lower molecular weight DNA fragments were not as strongly as are not retained as the higher molecular weight fragments. Increasing the electrical field strength results in lower molecular weight DNA restriction fragment being retained. In this manner, the electrical field strength can be adjusted to select the size of DNA fragment retained.

Figure 5A:
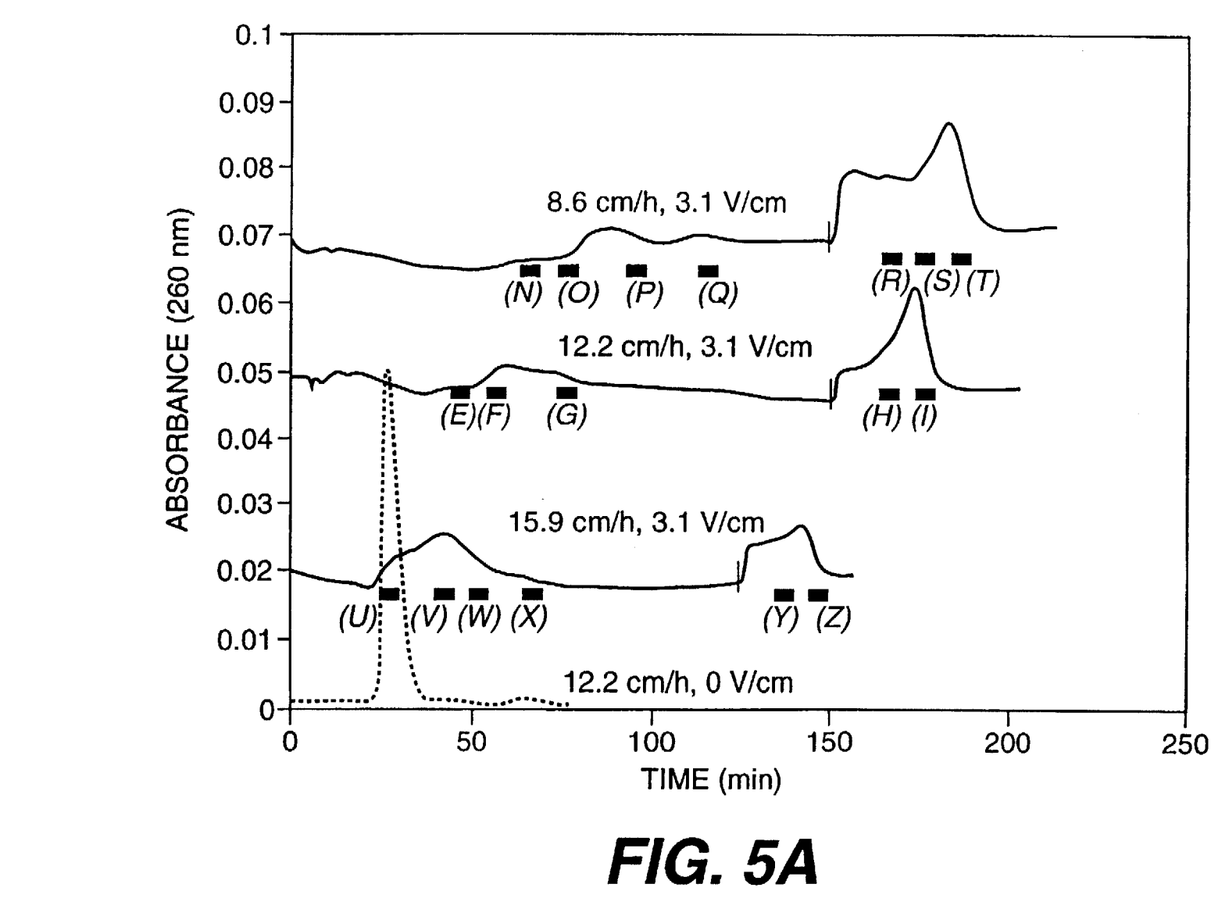
Figure 5B:
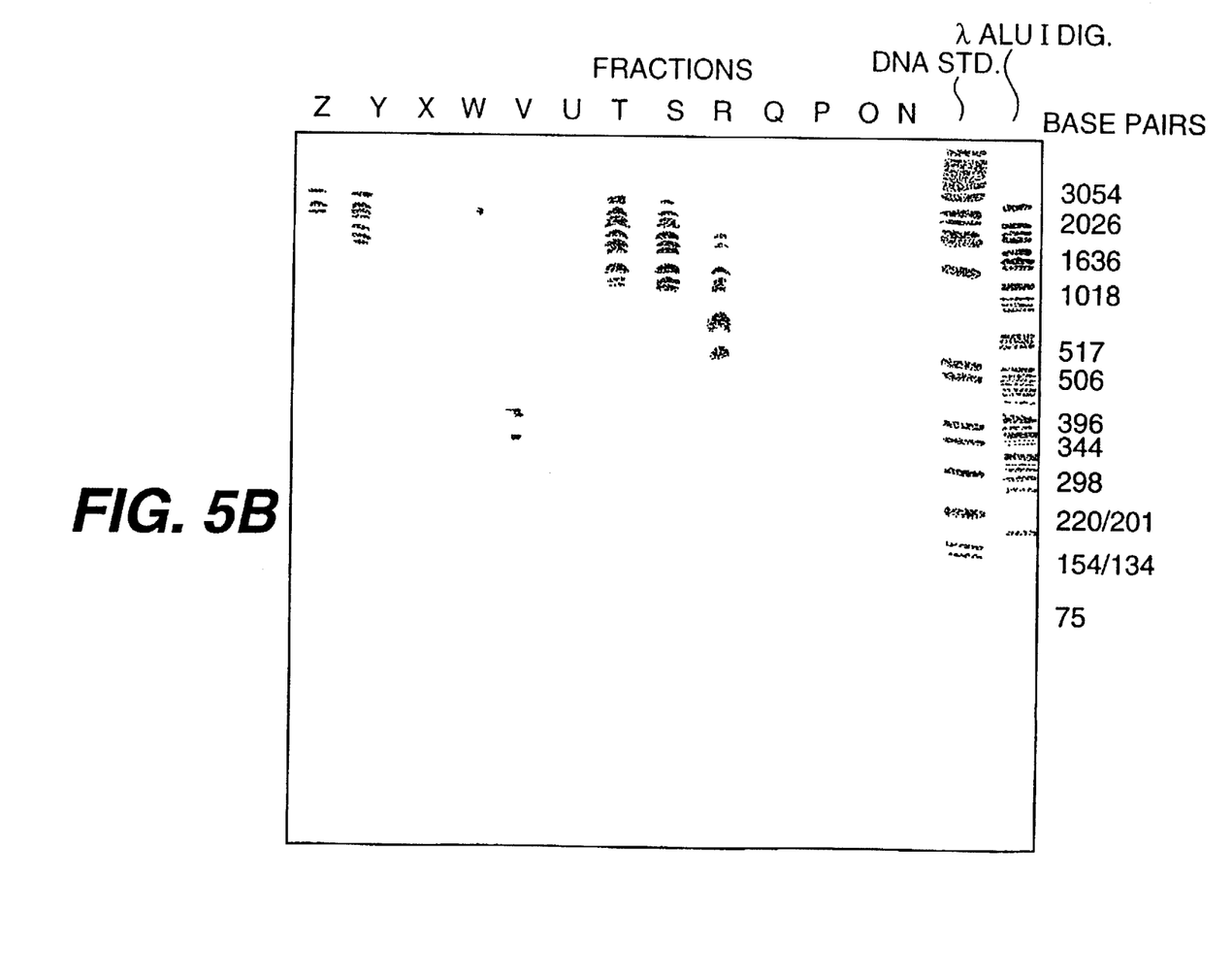

FIGS. 5A and B demonstrate the influence of flow rate on the retention of the Alu I restriction fragments while keeping the electrical field strength constant. At high flow rates the low molecular weight DNA fragments were not as strongly retained as the high molecular weight As flow rate is decreased the molecular weight of the DNA fragments retained on the column was also lowered. Table 1 contains a summary of the electrical field strength and flow rate dependence on the size of DNA fragment retained on the column in this set of experiments.

Although the present invention has been fully described in connection with the examples, it is to be noted that various changes and modifications are apparent to those skilled in the art. Such changes and modifications are to be understood as included within the scope of the present invention as defined by the appended claims, unless they depart therefrom.

Example 2

Retention of M-13 Bacteriophage Virus on Column Packed with Sephadex G-75

The experimental apparatus was the same as described in Example 1.

Virus

The samples were the filamentous virus M13. The virus used was M13, KM-4 that contained a 108 base inset in the M13 genome. M13 virus contains a circular single-stranded DNA of 6407 bases (kM-4, 6515 bases). M13 infects *E. coli* bacteria.

Titer of the Virus

The titer of the virus was determined by adding diluted samples to 0.2 ml overnight culture of *E. coli* K12 TG-1 (grown in LB media at 37° C.). The samples incubated at room temperature for 10 minutes and 3 ml of molten agarose (0.6% in LB broth) was added and poured on top of a 100 mm petri dish containing LB medium-1.5% agar (*ATCC Handbook*, First Edition, 1984, in R. Cote, ed. American Type Culture Collection, Rockville, Miss.). The petri dishes were incubated at 37° C. for 18 hours. The plaques were counted and plaque forming units (PFU) were calculated.

Samples

A sample containing $2.6 \times 10^{11}$ PFU in TGE buffer was applied to the column with either no field or a negative field of 50V (3.0 mA). Fractions (5 ml) were collected and the titer measured.

Results

M13 ($2.6 \times 10^{11}$ PFU) was applied to a column of Sephadex g-75 at a flow rate of 12 cm/hr without an electrical field. The virus came out of the column with the first absorbance peak at approximately 25 min. When the virus was applied to the column with a negative field of 3.5 V/cm and a flow rate of 12 cm/hr, the virus is retained on the column until the field is turned off. The amount of virus removed in the buffer which came out at the retention time of the first peak is reduced by a factor of $10^6$ (a reduction of 6 logs compared to the injection without an electrical field applied).

Example 3

Separation of Denatured (single-stranded) from Native (double-stranded) DNA

Method

A column (1.5×30 cm) was packed with Sephadex G-75. Buffer used was TGE as previously described. The flow rate used was 0.95 ml/min (linear velocity 0.538 cm/min) and the electrical field applied to the column was 1.19 V/cm. The sample applied to the column was 2.5 µg of λ DNA. A sample of µ DNA was denatured by boiling the sample (2.5 µg of λ DNA, in 0.25 ml of TGE) for 10 minutes followed by cooling to room temperature.

Results

Figure 6:
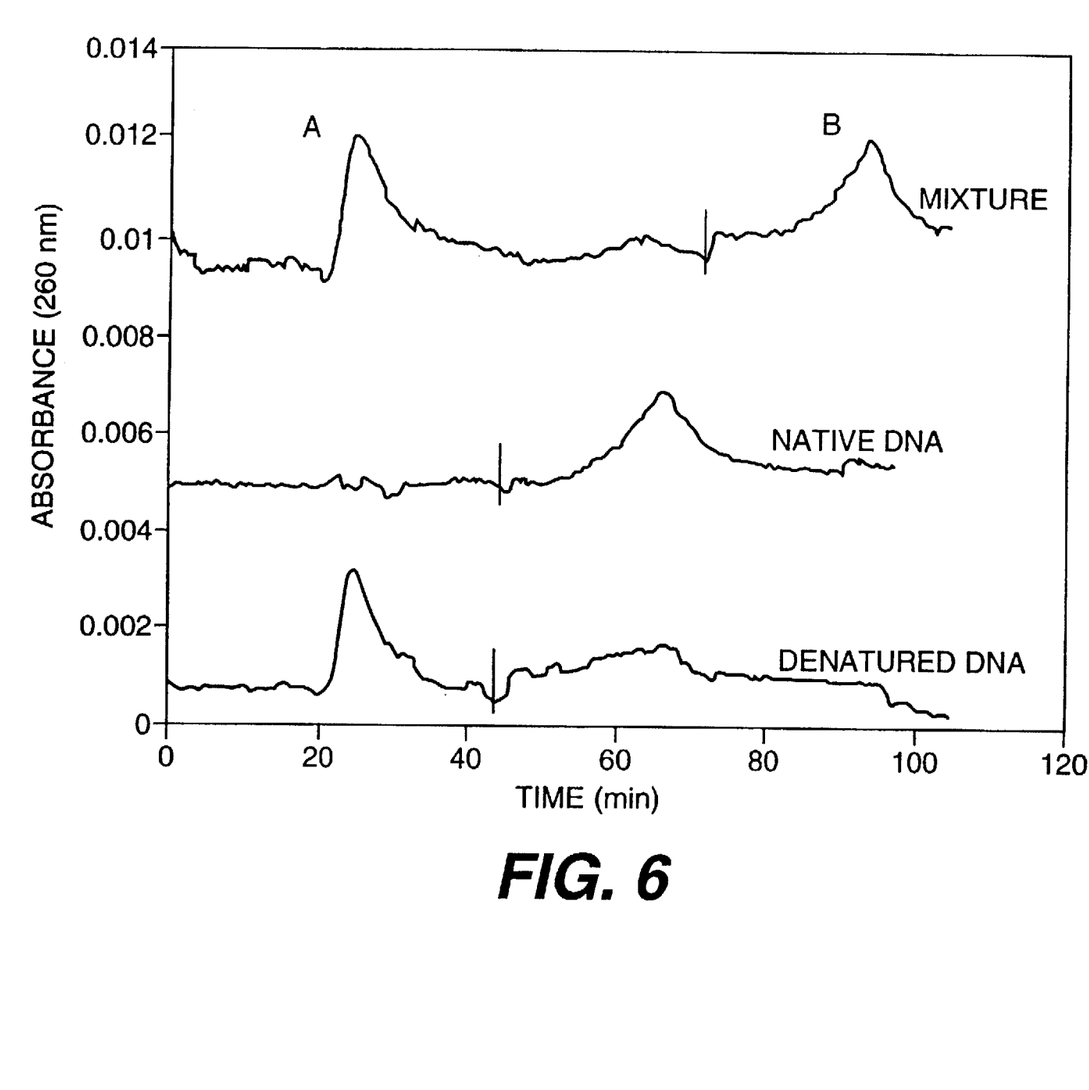

Samples of 2.5 µg of λ DNA, either denatured or native form were applied to the column and eluted as shown in FIG. 6. The denatured DNA eluted from the column with the field on. The native DNA did not elute from the column until the field was turned off (shown by the heavy vertical line in FIG. 6). A mixture of denatured and native λ DNA was also applied to the column under these conditions. The denatured DNA eluted in the peal labeled A in FIG. 6 and the native DNA eluted in the peak labeled B.

The column (1.5×30 cm) was packed with Sephadex G-75 and run with a flow rate of 0.95 ml/min. The samples (2.5 µg of λ DNA in 0.25 ml of TGE) was applied with a field of 1.2 V/cm and the field removed as indicated by the heavy vertical line.

Example 4

Separation of Super-coiled, Closed Circular, and Linear Plasmid DNA

Method

A column (1.5×30 cm) was packed with Sephadex G-75. Buffer used was TGE as previously described. The flow rate used was 0.48 ml/min (linear velocity 0.272 cm/min) and the electrical field applied to the column was 1.0 V/cm. The sample applied to the column was 6 µg of plasmid DNA. A sample of plasmid DNA was linearized by digestion with the restriction enzyme Eco RI. The plasmid used was pKL 502.

Results

Figure 7:
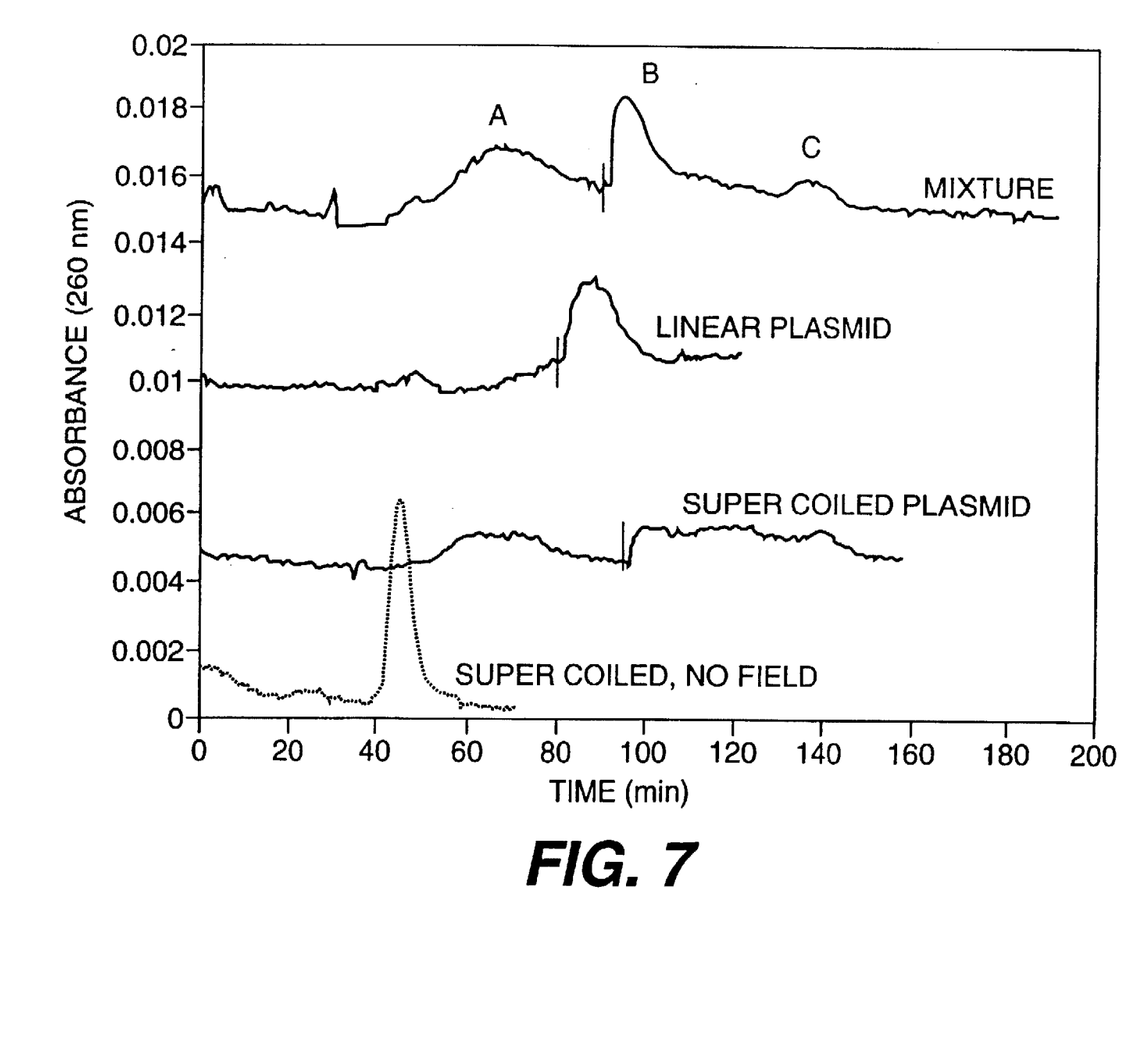

Samples of 6 µg of plasmid DNA either supercoiled, or linear plasmid were applied to the column and eluted as shown in FIG. 7. Most of the supercoiled plasmid DNA eluted from the column with the field on. Most of the linear plasmid DNA did not elute from the column until the field was turned off (shown by the heavy vertical line in FIG. A2). A mixture of super-coiled and linear plasmid DNA. was also applied to the column under these conditions. Most of the supercoiled DNA eluted in the peal labeled A in FIG. A2 and most of the linear DNA eluted in the peaks labeled B and C. Gel electrophoresis analysis indicated that most of the relaxed circular plasmid DNA was located in the peak labeled B.

The column (1.5×30 cm) was packed with Sephadex G-75 and run with a flow rate of 0.48 ml/min. The samples (6 µg of super-coiled or linear plasmid DNA) were applied with a field of 1.0 V/cm and the field removed as indicated by the heavy vertical line.

What is claimed is:

1. A method for separating nucleic acid material from a solution containing nucleic acid material comprising the steps of:

flowing a mixture comprising a buffer medium and a solution containing nucleic acid material through a chromatography media comprising porous beads, the nucleic acid material comprising a material selected from the group consisting of nucleic acids and viruses;

applying an electrical field to the mixture flowing through the chromatography media to retain a retained material on the chromatography media, the retained material consisting essentially of the nucleic acid material; and recovering the nucleic acid material from the chromatography media.

2. The method of claim 1, further comprising the step of lowering the pH of the mixture to prevent proteins contained in the mixture from being retained on the chromatography media when the electrical field is applied.

3. The method of claim 1, wherein the field strength of the applied electric field is from about 0.1 to 50 V/cm.

4. The method of claim 1, wherein the flow rate of mixture through the chromatography media is from about 0.1 to 200 cm/hr.

5. The method of claim 4, wherein the field strength of the applied electric field is from about 0.1 to 50 V/cm.

6. The method of claim 1, wherein the electric field is negative.

7. The method of claim 1, wherein the recovered nucleic acid material comprises at least one nucleic acid.

8. The method of claim 1, wherein the recovered nucleic acid material comprises at least one virus.

9. The method of claim 8, wherein the at least one virus comprises a M13 virus.

10. The method of claim 1, wherein the solution containing the nucleic acid material comprises in addition to the nucleic acid material at least one substance selected from the group consisting of proteins, carbohydrates and lipids.

11. The method of claim 1, wherein the solution containing the nucleic acid material comprises proteins in addition to the nucleic material.

12. The method of claim 1, further comprising the step of increasing the flow rate of the mixture through the chromatography media to increase a minimum size of the nucleic acid material retained on said chromatography media.

13. The method of claim 1, further comprising the step of decreasing the flow rate of the mixture through the chromatography media to decrease a minimum size of the nucleic acid material retained on said chromatography media.

14. The method of claim 1, wherein said flowing step comprises pulsing the mixture through the chromatography media.

15. The method of claim 1, wherein the recovered nucleic acid material comprises DNA.

16. The method of claim 15, wherein the DNA is selected from the group consisting of: double stranded DNA, single stranded DNA, linear DNA, circular DNA, supercoiled DNA and relaxed (closed circular) DNA.

17. The method of claim 1, wherein the chromatography media comprises a Sephadex column.

* * * * *